(12) United States Patent
Marshall

(10) Patent No.: US 9,940,738 B2
(45) Date of Patent: Apr. 10, 2018

(54) SYSTEM AND METHOD FOR REDUCING DATA TRANSMISSION VOLUME IN TOMOSYNTHESIS

(71) Applicant: HOLOGIC, INC., Bedford, MA (US)

(72) Inventor: Julian Marshall, Los Altos, CA (US)

(73) Assignee: HOLOGIC, INC., Marlborough, MA (US)

( * ) Notice: Subject to any disclaimer, the term of this patent is extended or adjusted under 35 U.S.C. 154(b) by 68 days.

(21) Appl. No.: 14/760,035

(22) PCT Filed: Jan. 9, 2014

(86) PCT No.: PCT/US2014/010911
§ 371 (c)(1),
(2) Date: Jul. 9, 2015

(87) PCT Pub. No.: WO2014/110283
PCT Pub. Date: Jul. 17, 2014

(65) Prior Publication Data
US 2015/0356757 A1    Dec. 10, 2015

Related U.S. Application Data

(60) Provisional application No. 61/750,840, filed on Jan. 10, 2013.

(51) Int. Cl.
*G06T 11/00* (2006.01)
*A61B 6/00* (2006.01)
(Continued)

(52) U.S. Cl.
CPC ............ *G06T 11/006* (2013.01); *A61B 6/025* (2013.01); *A61B 6/463* (2013.01); *A61B 6/502* (2013.01);
(Continued)

(58) Field of Classification Search
None
See application file for complete search history.

(56) References Cited

U.S. PATENT DOCUMENTS

| 4,907,156 A | 3/1990 | Doi et al. |
| 5,133,020 A | 7/1992 | Giger et al. |

(Continued)

FOREIGN PATENT DOCUMENTS

| JP | 2006-223449 | 8/2006 |
| JP | 2009-066306 | 4/2009 |

(Continued)

OTHER PUBLICATIONS

European Search Report for EP Application No. 14737752.7, dated Aug. 11, 2016 (7 pages).
(Continued)

*Primary Examiner* — Matthew Bella
*Assistant Examiner* — Brian Shin
(74) *Attorney, Agent, or Firm* — Vista IP Law Group, LLP

(57) ABSTRACT

A method for processing and communicating breast tissue image data includes obtaining image data of a patient's breast tissue, processing the image data to form a first subset thereof, transmitting the first subset of the image data to a user computer, receiving a user request from the user computer based on the one or more lower resolution images, processing the image data to form a second subset thereof, and transmitting the second subset of the image data to the user computer. The second subset of the obtained image data is responsive to the user request. The first and second subsets of obtained image data are sufficient to generate one or more respective lower and higher resolution images of respective portions of the patient's breast tissue.

30 Claims, 3 Drawing Sheets

(51) Int. Cl.
  *G06T 15/08* (2011.01)
  *G06T 7/00* (2017.01)
  *A61B 6/02* (2006.01)

(52) U.S. Cl.
  CPC .......... *A61B 6/5211* (2013.01); *A61B 6/5217* (2013.01); *A61B 6/563* (2013.01); *G06T 7/0012* (2013.01); *G06T 15/08* (2013.01); *A61B 6/469* (2013.01); *A61B 6/5223* (2013.01); *G06T 2200/04* (2013.01); *G06T 2207/30068* (2013.01); *G06T 2207/30196* (2013.01); *G06T 2210/41* (2013.01); *G06T 2211/436* (2013.01)

(56) References Cited

U.S. PATENT DOCUMENTS

| | | | |
|---|---|---|---|
| 5,343,390 | A | 8/1994 | Doi et al. |
| 5,491,627 | A | 2/1996 | Zhang et al. |
| 6,421,454 | B1 | 7/2002 | Burke et al. |
| 6,847,729 | B1 | 1/2005 | Clinch et al. |
| 7,577,282 | B2 | 8/2009 | Gkanatsios et al. |
| 7,606,801 | B2 | 10/2009 | Faitelson et al. |
| 7,702,142 | B2 | 4/2010 | Ren et al. |
| 7,760,924 | B2 | 7/2010 | Ruth et al. |
| 7,991,837 | B1 | 8/2011 | Tahan |
| 8,126,226 | B2 | 2/2012 | Bernard et al. |
| 8,571,289 | B2 | 10/2013 | Ruth et al. |
| 2006/0093207 | A1 | 5/2006 | Reicher et al. |
| 2007/0183564 | A1* | 8/2007 | Li .................. A61B 6/465 378/22 |
| 2007/0234239 | A1* | 10/2007 | Sylthe .................. G06F 3/1407 715/864 |
| 2007/0242868 | A1 | 10/2007 | Stanton et al. |
| 2012/0324397 | A1 | 12/2012 | Patz et al. |

FOREIGN PATENT DOCUMENTS

| WO | 2008/005868 | 1/2008 |
|---|---|---|
| WO | 2010/023580 | 3/2010 |
| WO | 2013123091 | 8/2013 |
| WO | 2014110283 | 7/2014 |

OTHER PUBLICATIONS

Giger et al., An "Intelligent" Workstation for Computer-aided Diagnosis in RadioGraphics, May 1993, pp. 647-656 (10 pages).

International Search Report and Written Opinion for International Application No. PCT/US2014/010911. Applicant Hologic, Inc., dated Jun. 3, 2014 (9 pages).

Giger et al., Development of a "smart" workstation for use in mammography, in Proceedings of SPIE, Medical Imaging V: Image Processing, vol. 1445, Feb. 27-Mar. 1, 1991, pp. 101-103 (4 pages).

Office action dated Aug. 31, 2017 for JP Application No. 2015-552780, Applicant Hologic, Inc., including translation provided by Japanese Associate 19 pages.

English language Abstract for Japanese laid open publication No. 2009-223449, published Apr. 2, 2009, 1 page.

English language Abstract for Japanese laid open publication No. 2006-066306, published Aug. 31, 2006, 1 page.

* cited by examiner

SYSTEM AND METHOD FOR REDUCING DATA TRANSMISSION VOLUME IN TOMOSYNTHESIS

RELATED APPLICATION DATA

This application is a National Phase entry under 35 U.S.C § 371 of International Patent Application No. PCT/US2014/010911, having an international filing date of Jan. 9, 2014, which claims the benefit of priority under 35 U.S.C. § 119 to U.S. Provisional Patent Application No. 61/750,840, filed Jan. 10, 2013, which is hereby incorporated by reference in its entirety.

FIELD

The inventions disclosed herein pertain to breast imaging using tomosynthesis, and more specifically to systems and methods for obtaining, processing, communicating, and navigating a tomosynthesis data set or a subset thereof.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Tomosynthesis systems have recently been developed for breast cancer screening and diagnosis. In particular, Hologic, Inc. (www.hologic.com), has developed a fused, multimode mammography/tomosynthesis system that acquires one or both types of mammogram and tomosynthesis images, either while the breast remains immobilized or in different compressions of the breast. Other companies have proposed the introduction of systems which are dedicated to tomosynthesis imaging; i.e., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may be displayed along with tomosynthesis projection or reconstructed images, in order to assist in screening and diagnosis.

While tomosynthesis systems provide more data to users to facilitate detection and characterization of features of interest ("FOI"), the increased amount of data can sometimes strain data communication channels and data storage facilities. Further, generating multiple 2D and 3D images for tomosynthesis increases demands on computational resources. Accordingly, there exists a need for tomosynthesis systems and methods that minimize the amount of generated, stored, and communicated data.

SUMMARY

In one embodiment of the disclosed inventions, a method for processing and communicating breast tissue image data is provided. The method includes obtaining image data of a patient's breast tissue, processing the image data of the patient's breast tissue to form a first subset thereof, and transmitting the first subset of the image data to a user computer. The method also includes receiving a user request for higher resolution images from the user computer based on the one or more lower resolution images, processing the image data of the patient's breast tissue to form a second subset thereof, and transmitting the second subset of the image data to the user computer. The second subset of the image data is responsive to the user request. The first subset of image data is sufficient to generate one or more lower resolution images of at least a portion of the patient's breast tissue and the second subset of image data is sufficient to generate one or more higher resolution images of the patient's breast tissue.

In another embodiment of the disclosed inventions, a method for processing, displaying and navigating breast tissue image data is provided. The method includes receiving a first subset of image data of a patient's breast tissue from an image acquisition system, processing the first subset of image data to generate one or more lower resolution images of the patient's breast tissue, and displaying the one or more lower resolution images. The method also includes receiving a user request for higher resolution images of the patient's breast tissue, transmitting the user request to the image acquisition system, and receiving a second subset of image data of the patient's breast tissue from the image acquisition system, where the second subset of image data is responsive to the user request. Further, the method includes processing the second subset of image data to generate one or more higher resolution images of the patient's breast tissue, and displaying the one or more higher resolution images.

In still another embodiment of the disclosed inventions, a system for processing and communicating breast tissue image data includes an image acquisition system configured to communicate with a user computer. The image acquisition system is configured to obtain image data of a patient's breast tissue, form a first subset of the image data, and form a second subset of image data of the patient's breast tissue in response to a user command received from the user computer. The first subset of image data is sufficient to generate one or more lower resolution images of at least a portion of the patient's breast tissue, and the second subset of image data is sufficient to generate one or more higher resolution images of at least a portion of the patient's breast tissue.

In yet another embodiment of the disclosed inventions, a system for processing, displaying and navigating breast tissue image data includes a user computer configured to communicate with an image acquisition system, at least one display operatively coupled to the user computer, and a user input device operatively coupled to the user computer. The user computer is configured to receive a first subset of image data of a patient's breast tissue from an image acquisition system, process the first subset of image data to generate one or more lower resolution images of the patient's breast tissue, and display the one or more lower resolution images on the display. The user computer is also configured to receive a user request for higher resolution images of the patient's breast tissue through the user input device, and transmit the user request to the image acquisition system. The user computer is also configured receive a second subset of image data of the patient's breast tissue from the image acquisition system responsive to the user request, process the second subset of image data to generate one or more higher resolution images of the patient's breast tissue, and display the one or more higher resolution images on the display.

In some embodiments, the image data includes acquired or synthesized X,Y coordinate slices at differing z axis locations of the patient's breast. A resolution of the one or more lower resolution images may be sufficient to detect a potential abnormality or a region of interest in the patient's breast tissue. A resolution of the one or more higher resolution images may be sufficient to characterize a potential abnormality or a region of interest in the patient's breast tissue.

In some embodiments, the resolution of the one or more higher resolution images is in the range of about 50 microns to about 140 microns, in the range of about 50 microns to about 85 microns, and/or about 70 microns. The resolution of the one or more higher resolution images may be about 1.5 times to 5 times the image resolution of the one or more lower resolution images. The resolution of the one or more higher resolution images may be about double the image resolution of the one or more lower resolution images.

In some embodiments, the image data includes one or more images selected from a group consisting of tomosynthesis projection images, tomosynthesis reconstruction slices, mammography images, contrast enhanced mammography images, synthesized 2D images, and combinations thereof. The first subset of the image data may be sufficient to generate one or more lower resolution images of the patient's breast in which a feature, object or region is automatically highlighted. The one or more low resolution images may have a characteristic different from the characteristic of the one or more high resolution images. The characteristic may be selected from the group consisting of slice thickness, pitch, yaw, and tilt.

In some embodiments, the user request identifies an object or region of interest in the one or more lower resolution images. In some embodiments, the user request identifies one or more lower resolution images.

These and other aspects and embodiments of the disclosed inventions are described in more detail below, in conjunction with the accompanying figures.

BRIEF DESCRIPTION OF FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

Figure 1:
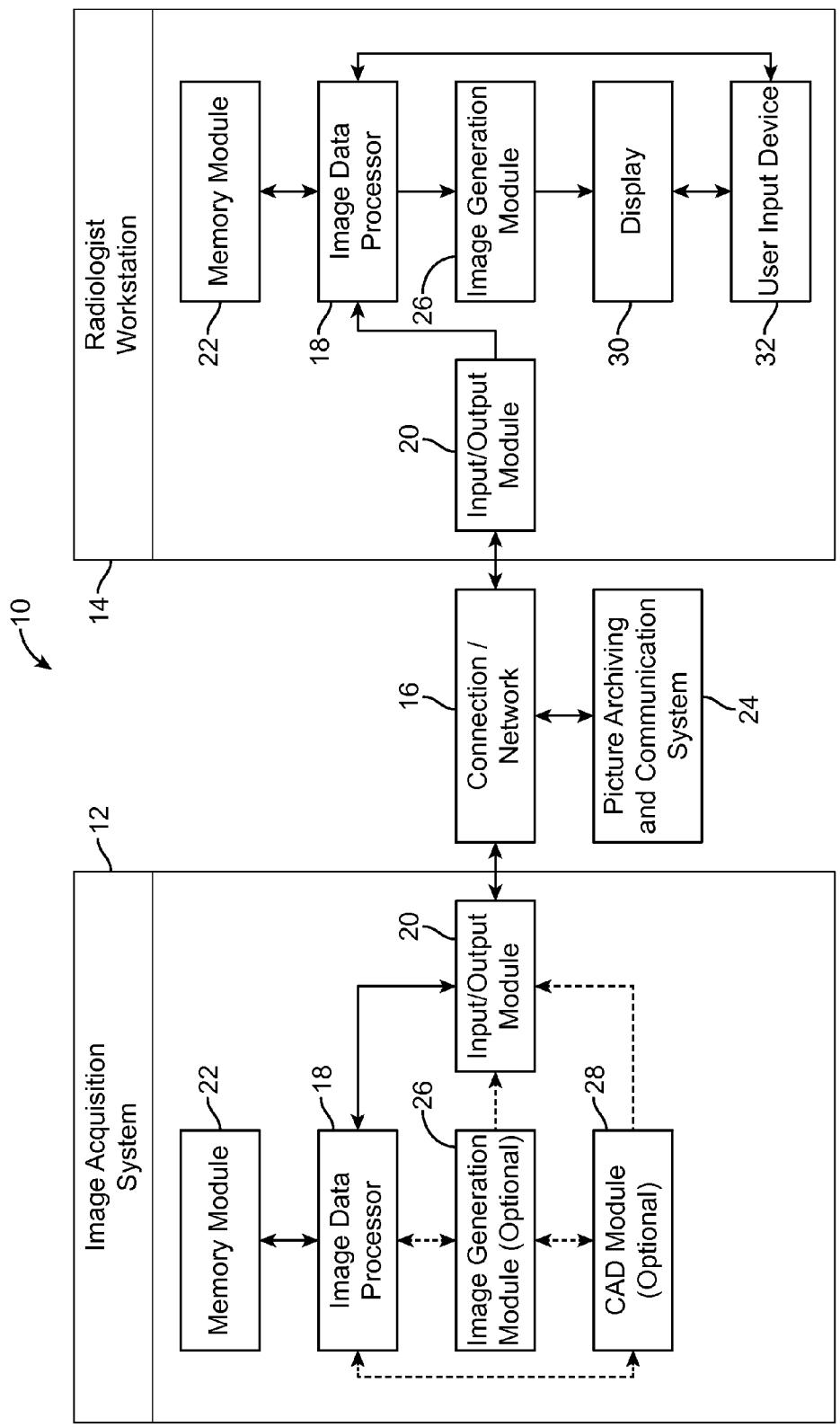
FIG. 1 is a block diagram illustrating a tomosynthesis image processing and navigating system according to one embodiment.

Other and further aspects and features of embodiments of the disclosed inventions will become apparent from the ensuing detailed description in view of the accompanying figures.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the terms "about" or "approximately," whether or not explicitly indicated. The terms "about" and "approximately" generally refers to a range of numbers that one of skill in the art would consider equivalent to the recited value (i.e., having the same function or result). In many instances, he terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

The following abbreviations shall have the following definitions throughout this patent specification and the accompanying claims:

Mp refers to a conventional mammogram or contrast enhanced mammogram, which are two-dimensional (2D) projection images of a breast, and encompasses both a digital image as acquired by a flat panel detector or another imaging device, and the image after conventional processing to prepare it for display and/or storage or other use.

Tp refers to an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display and/or storage or other use.

Tr refers to an image that is reconstructed from tomosynthesis projection images Tp, for example, in the manner described in one or more of U.S. Patent Application Publication No. 2010/0135558, and U.S. Pat. Nos. 7,760,924, 7,606,801, and 7,577,282, the disclosures of which are fully incorporated by reference herein in their entirety, wherein a Tr image represents a slice of the breast as it would appear in a projection x ray image of that slice at any desired angle, not only at an angle used for acquiring Tp or Mp images.

Ms refers to synthesized 2D images, which simulate mammography images, such as a craniocaudal (CC) or mediolateral oblique (MLO) images, and are constructed using tomosynthesis projection images Tp, tomosynthesis reconstructed images Tr, or a combination thereof. Examples of methods that may be used to generate Ms images are described in the above-incorporated U.S. Patent Application Publication No. 2010/0135558, and U.S. Pat. No. 7,760,924.

The terms Tp, Tr, Ms and Mp each encompasses information, in whatever form, that is sufficient to describe the respective image for display, further processing, or storage. The respective Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to x rays of corresponding volumes in the breast, i.e., voxels or columns of tissue. In a preferred embodiment, the geometry of the tomosynthesis images (Tr and Tp), mammography images (Ms and Mp) are matched to a common coordinate system, as described in U.S. Pat. No. 7,702,142, the disclosure of which is hereby incorporated by reference in its entirety. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

FIG. 1 depicts a tomosynthesis image processing and review system ("tomosynthesis system") 10 according to one embodiment. The tomosynthesis system 10 includes an image acquisition system 12 operatively coupled to a radiologist workstation 14 by a data connection such as a "network" 16. In some embodiments, the image acquisition system is also known as a "host computer," and the radiologist workstation is also known as a "user computer." In some embodiments, the "host computer" has more processing power than the "user computer," and is operatively coupled to a plurality of "user computers" to facilitate simultaneous review by a plurality of users. The "host computer" functions as a data server. The "user computer" may be a workstation, a personal computer, or a tablet computer. The tomosynthesis system 10 also includes a DICOM-compliant Picture Archiving and Communication System (PACS) storage device 24 connected to the image acquisition system 12 and the radiologist workstation 14 through the network 16.

The image acquisition system 12 can include a tomosynthesis image acquisition device (e.g., an X-ray, not shown), or it can be a separate computer optimized for image processing. The radiologist workstation 14 includes one or more displays and a user input device 32 to facilitate user interaction with the tomosynthesis data. The user may be any trained observer, such as a reader, a technician, or a radiologist. The image acquisition system 12 and the radiologist workstation 14 can be located adjacent to each other. Alternatively, the image acquisition system 12 and the radiologist workstation 14 can be separated from each other by a significant distance.

The data connection/"network" 16 may include two wired or wireless local area networks connected by one or more communication networks traversing large distances. Such multiple network connections 16 can only communicate as fast as the slowest network in the connection 16, taking into account the other traffic on each network.

The image acquisition system 12 includes an image data processor 18 connected to an input/output module 20 and a memory module 22. While the depicted image acquisition system 12 includes a memory module 22, the memory module 22 may be located outside of the image acquisition system 12. In fact, the memory module 22 may be connected to the image acquisition system 12 by another connection/"network" over a large distance. In such tomosynthesis systems 10, whenever the image acquisition system 12 accesses (reads from and/or writes to) the memory module 22, traffic on this other connection/"network" increases. The input/output module 20 is configured to exchange data with another processor through a network 16.

The image acquisition system 12 can optionally include an image generation module 26 configured to process raw tomosynthesis data into data that can be displayed as an image with a minimal amount of further processing. The image acquisition system 12 can also optionally include a computer aided detection ("CAD") module 28. The CAD module 28 is configured to process image data and identify FOIs therein. The function of the CAD module 28 is described, for example, in the references cited herein and in PCT patent application number PCT/US2013/025993, the disclosure of which is hereby incorporated by reference in its entirety.

The radiologist workstation 14 includes an image data processor 18 connected to an input/output module 20 and a memory module 22. While the depicted radiologist workstation 14 includes a memory module 22, the memory module 22 may be located outside of, and connected by another network, to the radiologist workstation 14. The input/output module 20 is configured to exchange data with another processor (for instance, with the image data processor 18 of the image acquisition system 12) through a network 16.

The radiologist workstation 14 also includes an image generation module configured to process image data to generate an image for display on a display 30 of the radiologist workstation 14. The display 30 preferably includes more than one screen to present visual data to a user. The display 30 is also configured to present user interface objects to the user. The display 30 may be part of a standard acquisition workstation, or of a standard (multi-display) review station that is physically remote from the acquisition system (not shown). In some embodiments, a display 30 connected via a communication network may be used, for example, a display of a personal computer or of a so-called tablet, smart phone or other hand-held device. In any event, the display 30 of the radiologist workstation 14 is preferably able to display tomosynthesis images concurrently, e.g., in separate side-by-side monitors. However, some embodiments may still be implemented with a single display monitor, by toggling between images.

The radiologist workstation 14 also includes a user input device 32, such as, but not limited to, a pointing device (e.g., a mouse or a trackball), a touchscreen, a voice recognition device, and/or an eye movement sensing device.

Figure 2:
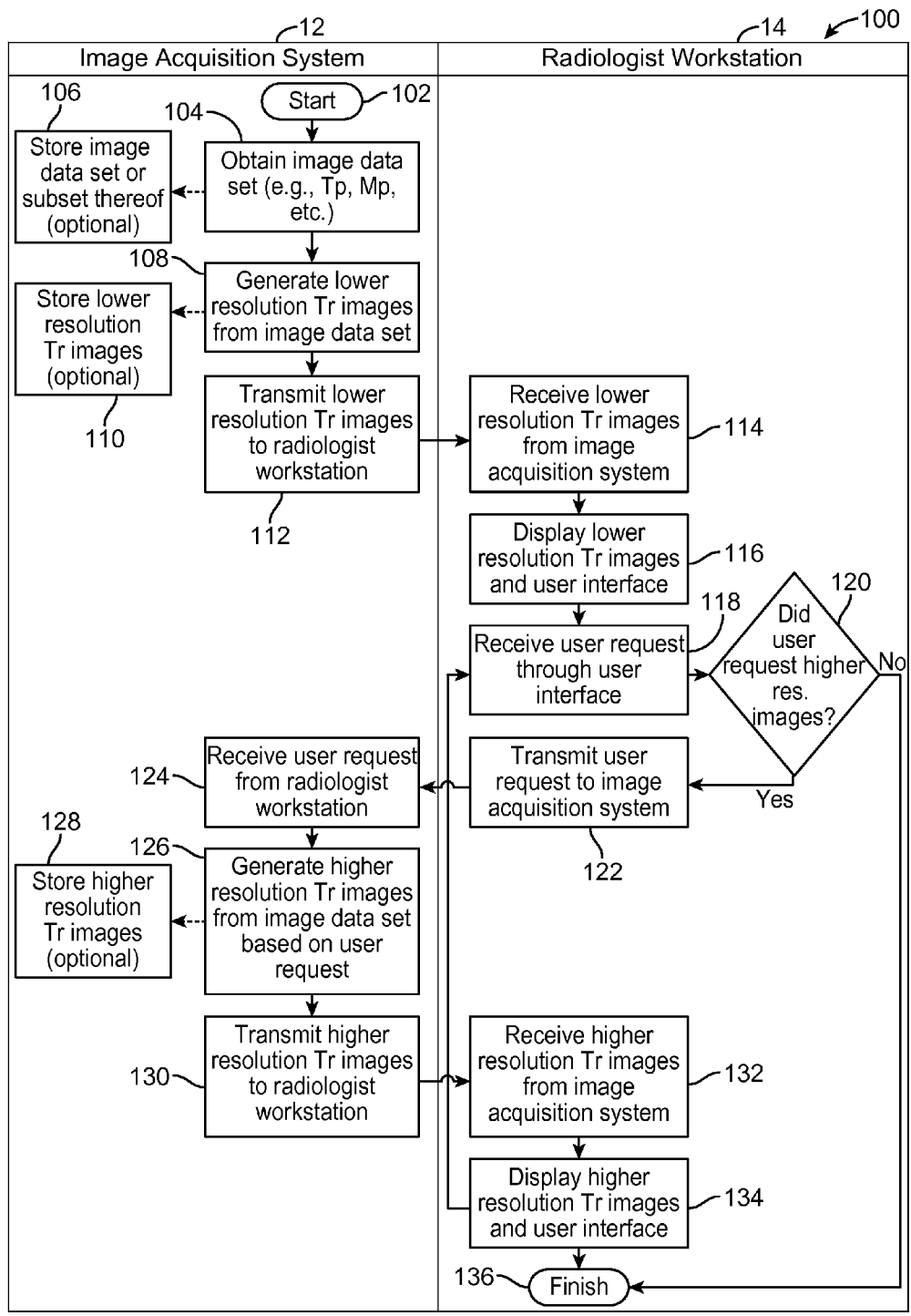
FIG. 2 is a flow diagram illustrating exemplary steps performed during a tomosynthesis image processing, communicating, and navigating method according to one embodiment.

Having described the tomosynthesis system 10, a method 100 of using the tomosynthesis system 10 to process and review a tomosynthesis data set according to one embodiment will now be described with reference to FIG. 2. FIG. 2 illustrates the steps of a tomosynthesis data processing and review method 100, which incorporates the presently disclosed tomosynthesis system. It should be understood that, while FIG. 2 illustrates a particular embodiment of a flow diagram with certain processes taking place in a particular serial order or in parallel, various other embodiments are not limited to the performance of the image processing and display steps in any particular order, unless so specified.

The illustrated method 100 is carried out on an image acquisition system 12 and a radiologist workstation 14. This method 100 provides the most advantages in embodiments where the image acquisition system 12 and the radiologist workstation 14 reside in respective distant locations. In such embodiments, the computers 12, 14 are connected by one or more networks 16 (e.g., two wired or wireless local area networks connected by one or more communication networks traversing large distances).

The illustrated method begins at the "start" icon 102 on the flow chart (FIG. 2). In other embodiments, the method begins when a user at the radiologist workstation 14 initiates a review process. In still other embodiments, the method begins when the image acquisition system 12 is notified about available image data.

In any of the above-described embodiments, the image acquisition system 12 obtains an image data set at step 104. The image data set represents the results of one or more tomosynthesis scans on one patient. For instance, the image data set can be Tp or Mp data. The image data set can be obtained directly from a tomosynthesis imaging device or from a memory module in which previously obtained image data has been stored. For instance, the image acquisition system 12 can obtain image data from legacy mammogram images in a storage device, such as a DICOM-compliant Picture Archiving and Communication System (PACS) storage device 17 connected to the image acquisition system 12 through a network 16.

The image acquisition system 12 can optionally store the obtained image data set or a selected subset thereof in a memory module 22 at step 106. Typically, the image data set is stored for an amount of time sufficient for a user to review and revisit the data (e.g., two months). The image data set is not typically stored indefinitely and may be purged to make room for new data after sufficient time has elapsed. Locating the tomosynthesis imaging device, the image acquisition system 12, and the memory module 22 within the same local area network increases the speed of image data communication on the image acquisition side of the method. However, some embodiments include memory modules that are separated from the tomosynthesis imaging device and the image acquisition system 12 by large distances. In such embodiments, any obtained or stored image data must travel through another network, slowing the review process.

At step 108, the image acquisition system 12 generates lower resolution images from the image data set. For instance, obtained Tp images can be reconstructed into reconstructed image "slabs" Tr, representing breast slices of selected thickness and at selected orientations, as disclosed in the above-incorporated patents and application publications. The method may also include highlighting FOI in the generated lower resolution images. For the purpose of this patent specification, a feature or object of interest in a source image may be considered a "most relevant" feature based upon the application of one or more CAD algorithms to the collective source images, wherein the CAD algorithms assign numerical values, weights or thresholds, to pixels or regions of the respective source images based upon identified/detected objects and features of interest within the respective region or between features. Alternatively, in instances when the lower resolution images are generated directly from the obtained image data without CAD assistance, simply the pixel value, weight or other threshold associated with a pixel or region of the image. The objects and features of interest may include, for example, spiculated lesions, calcifications, and the like. Various systems and methods are currently well known for computerized detection of abnormalities in radiographic images, such as those disclosed by Giger et al. in RadioGraphics, May 1993, pp. 647-656; Giger et al. in Proceedings of SPIE, Vol. 1445 (1991), pp. 101-103; U.S. Pat. Nos. 4,907,156, 5,133,020, 5,343,390, and 5,491,627, each of which being hereby incorporated by reference in its entirety.

"Generating a lower resolution image" refers to generating information that is sufficient to describe the lower resolution image for display and does not require actually displaying a lower resolution image. The resolution of lower resolution images varies depending on the capabilities of the image acquisition device and system. Typically, the lower resolution images have about ⅔ to about ⅕, and preferably about half the image resolution of higher resolution images (described below). The image resolution is inversely proportional to the resolution measured in pixel size (microns), such that doubling the image resolution is equal to halving the pixel size (microns). In some embodiments, these lower resolution Tr images have a resolution of about 100 µm to about 280 µm, preferably about 100 µm to about 170 µm, and more preferably about 100 µm. However, the claims are not limited to these ratios of higher and lower resolutions and specific lower resolution values.

Lower resolution Tr images are suitable for detection of FOIs because the smallest objects that should be detected, examined, and characterized, according to current standards of care for mammography, range from 150 µm to 500 µm in size. FOI include objects or regions of interest and are potential abnormalities such as calcifications and masses. The goal of the detection phase of image data review is to enable the user to notice or observe these small objects/FOIs. Therefore, the lower resolution Tr images are also called "detection images." While the illustrated embodiment includes generating Tr images, the claims are not so limited. The claims encompass methods involving any images that are sufficient for detection of clinically relevant FOIs in accordance with the standard of care for mammography.

The image acquisition system 12 can optionally store the lower resolution images in a memory module 22 at step 110. The lower resolution images are stored for an amount of time consistent with applicable rules and regulations in the jurisdiction, up to, and including, indefinitely. The smaller size of the lower resolution images reduces the amount of data storage space and the amount of network traffic required to comply with the rules and regulations, when compared to storing higher resolution images of the entire tomosynthesis volume.

At step 112, the image acquisition system 12 transmits the generated lower resolution images to the radiologist workstation 14. This transmission step uses a smaller amount of bandwidth in the multiple network connection 16 between the image acquisition system 12 and the radiologist workstation 14, when compared to transmitting higher resolution images of the entire tomosynthesis volume, because the transmitted images have a lower resolution than the maximum resolution allowed by the obtained image data set. At step 114, the radiologist workstation 14 receives the transmitted lower resolution images from the image acquisition system 12. While the illustrated embodiment includes transmission and reception of images, the claims are not so limited. The claims encompass methods involving transmission and reception of image data from which images may be generated.

At step 116, the radiologist workstation 14 displays the lower resolution images, along with a user interface, on a display 30 to facilitate user interaction with the lower resolution image. This user interaction may involve other user input devices 32 (e.g., a mouse or a trackball) that are elements of the radiologist workstation 14.

After the detection phase of image data review, tomosynthesis image review continues with the characterization phase. The goal of the characterization phase is to facilitate user identification and categorization of the small objects previously noticed or observed in the detection phase. In many cases, the lower resolution Tr images may be clinically sufficient to not only detect, but also to characterize the FOIs. For instance, benign calcifications are typically rounder and larger than malignant calcifications. In some cases, a 100 µm resolution image will be sufficient to make that clinical determination (in accordance with the standard of care for mammography) that a large and round calcification is benign. In such cases, no higher resolution image data is required.

In other cases, additional (higher resolution) images are required to characterize the detected FOIs. In such cases, the user can interact with the displayed user interface and the user input device 32 to provide user requests to the radiologist workstation. Users may request higher resolution images of a specified subset of the tomosynthesis volume or the entire volume. These higher resolution images may correspond to some or all of the lower resolution images. The user request may be communicated in the form of 3D Cartesian coordinates or a point in 3D space and a radius, for instance. The user request may also include yaw/pitch/tilt information that connotes reconstruction in different planes with more degrees of freedom. Accordingly, the requested higher resolution images may differ from the displayed lower resolution images in slice thickness, pitch, yaw, and/or tilt. The user can communicate the user request by pointing to, hovering over, or otherwise indicating, one or more lower resolution images, or one or more FOIs (highlighted or not) on a lower resolution image.

Various embodiments include many different mechanisms for selection of the features of interest; although it is to be understood that the claims are not limited to those described herein. For example, the selection of a region or area within a low resolution image may include a selection of a CAD mark, or alternatively a selection of a particular feature of interest to the reviewer.

Selection Using CAD Marks:

If the lower resolution image is presented with a CAD overlay, the CAD overlay may include CAD marks derived from the obtained image data. CAD marks derived from 3D data generally include, as part of the data object associated with the mark, identifiers of one or more slices which contributed to the generation of the 3D mark. When the lower resolution image is overlaid with 3D CAD data, selection of the CAD mark results in the generation and retrieval of higher resolution images corresponding to the series of slices that contributed to the mark, or may be limited to the portion of those high resolution slices that span the detected region within each image slice. In one embodiment, the central image slice is first displayed; in alternate embodiments, the image slice having the highest weight is first displayed; in further alternate embodiments, the image slice having the sharpest image features is first displayed; and in a still further alternate embodiment, the image slice having the least visual noise (i.e., the clearest image) is first displayed.

Selection by Objects of Interest:

As an alternate to selecting by CAD marks, a mechanism is provided for allowing a user to select any object or location on a low resolution image, for example, a feature of interest, such as any abnormality or irregularity in the image. In one embodiment, the user or system may select a region, using for example a mouse click for a single pixel area, or a click and drag action to select a larger region. Alternatively, the user may be provided with a selection of graphical frames of various or variable sizes, and have the ability to move the frame to different locations within a lower resolution image to select areas when it is desired to view higher resolution image slices that display the features of interest.

The radiologist workstation 14 receives the provided user request through the user interface at step 118. At step 120, the radiologist workstation 14 determines whether it has received a user request for one or more higher resolution images. If the radiologist workstation 14 did not receive such a request, the illustrated method concludes at the "finish" icon 136 on the flow chart. If the radiologist workstation did receive a request for higher resolution images, the radiologist workstation 14 transmits the user request calling for higher resolution images to the image acquisition system 12 at step 122. The user request is transmitted through the multiple network connection 16 between the radiologist workstation 14 and the image acquisition system 12. Transmission of the user request uses a very small amount of bandwidth in the multiple network connection 16 because the user request is a small list of commands. The image acquisition system 12 receives the user request at step 124.

At step 126, the image acquisition system 12 generates the requested higher resolution images from the image data set based on the received user request. The resolution of higher resolution images varies depending on the capabilities of the image acquisition device and system. Typically, the higher resolution images have about 1.5 to about 5 times, and preferably about twice the image resolution of lower resolution images (described above). In some embodiments, these higher resolution images can be Tr images at a resolution of about 50 µm to about 140 µm, preferably about 50 µm to about 85 µm, and more preferably about 70 µm, but are not limited to either Tr images, specific ratios of higher to lower resolutions, or specific resolutions.

Higher resolution Tr images are suitable for characterization of the detected FOIs, because the resolution of the images allows them to clearly depict the FOIs and their features, which are used for characterization (e.g., border shape, inclusions, etc.) Therefore, the higher resolution Tr images are also called "characterization images." The lower and higher resolution images may be actual images, reconstructed images, and/or a combination of the two. The method may also include highlighting FOI in the generated higher resolution images.

The image acquisition system 12 can optionally store the higher resolution images in a memory module 22 at step 128. The lower resolution images are stored for an amount of time for an amount of time consistent with applicable rules and regulations, up to, and including, indefinitely. Embodiments in which the user requests only a subset of the tomosynthesis volume reduce the amount of data storage space required to comply with the rules and regulations, compared to storing higher resolution images of the entire tomosynthesis volume.

At step 130, the image acquisition system 12 transmits the generated higher resolution images, in accordance with the user request, to the radiologist workstation 14. As with data storage in step 128, embodiments in which the user requests only a subset of the tomosynthesis volume reduce the amount of bandwidth used for data transmission compared to transmitting higher resolution images of the entire tomosynthesis volume.

The amount of data stored and the amount of data transmitted in steps 128 and 130, respectively, can be further reduced by avoiding storage and/or transmission of higher resolution image data that is duplicative of other higher resolution image data that either will be or already has been stored and/or transmitted. Accordingly, when higher resolution Tr images are generated in step 126, portions of the higher resolution Tr images that are duplicative of portions of other higher resolution Tr images previously generated will be replaced with data calls that identify the duplicated portions of the previously generated higher resolution Tr images. In this manner, the volume of the higher resolution Tr images to be generated, transmitted, and/or stored is reduced in size. The volume of the higher resolution Tr images depends on the user input received at step 118, and may include up to all image slices in the image data set.

At step 132, the radiologist workstation 14 receives the transmitted higher resolution images from the image acquisition system 12. While the illustrated embodiment includes transmission and reception of images, the claims are not so limited. The claims encompass methods involving transmission and reception of less processed image data from which images may be generated with additional processing.

At step 134, the radiologist workstation 14 displays the higher resolution images, along with a user interface, on a display 30 to facilitate user interaction with the higher resolution images. Using the displayed user interface and user input devices 32, the user can make additional user requests for more higher resolution images, including, and up to, higher resolution images of the entire tomosynthesis volume. The radiologist workstation 14 receives the user request at step 118. If the radiologist workstation 14 determines whether it has received a user request for one or more higher resolution images at step 120, the higher resolution image generation, transmission, and display steps are repeated at steps 122, 124, 126, 128, 130, 132, and 134, until no further user requests are received. At that time, the illustrated method concludes at the "finish" icon 136 on the flow chart (FIG. 2).

In some embodiments, the image acquisition system 12 generates a complete set of higher resolution Tr images after the image data set is obtained at step 104. In still other embodiments, the image acquisition system 12 generates a set of higher resolution Tr images that contain CAD identified FOIs after the image data set is obtained at step 104. These embodiments are suitable for tomosynthesis systems 10 with powerful image data processors 18 and large memory module 22 for temporary storage of the generated higher resolution Tr images. Such embodiments conserve bandwidth on the networks 16 coupling the image acquisition system 12 to the radiologist workstation 14 by sending higher resolution Tr images to the radiologist workstation 14 only after a user reviews lower resolution Tr images and sends a user request through the radiologist workstation 14. The lower resolution Tr images may also include CAD markers identifying the FOIs to facilitate review. Pre-generating higher resolution Tr images accelerates system response time and the review process.

In other embodiments, the image acquisition system 12 generates a set of higher resolution Tr images that contain CAD identified FOIs after the image data set is obtained at step 104. These FOI containing higher resolution Tr images are transmitted to the radiologist workstation 14, for user review. After reviewing the FOI containing higher resolution Tr images, the user can send a user request for additional higher resolution Tr images. This embodiment partially reduces the amount of data generated, stored, and transmitted by generating higher resolution Tr images of only image slices containing CAD identified FOIs. Generating and transmitting FOI containing higher resolution Tr images further accelerates system response time and the review process.

Figure 3:
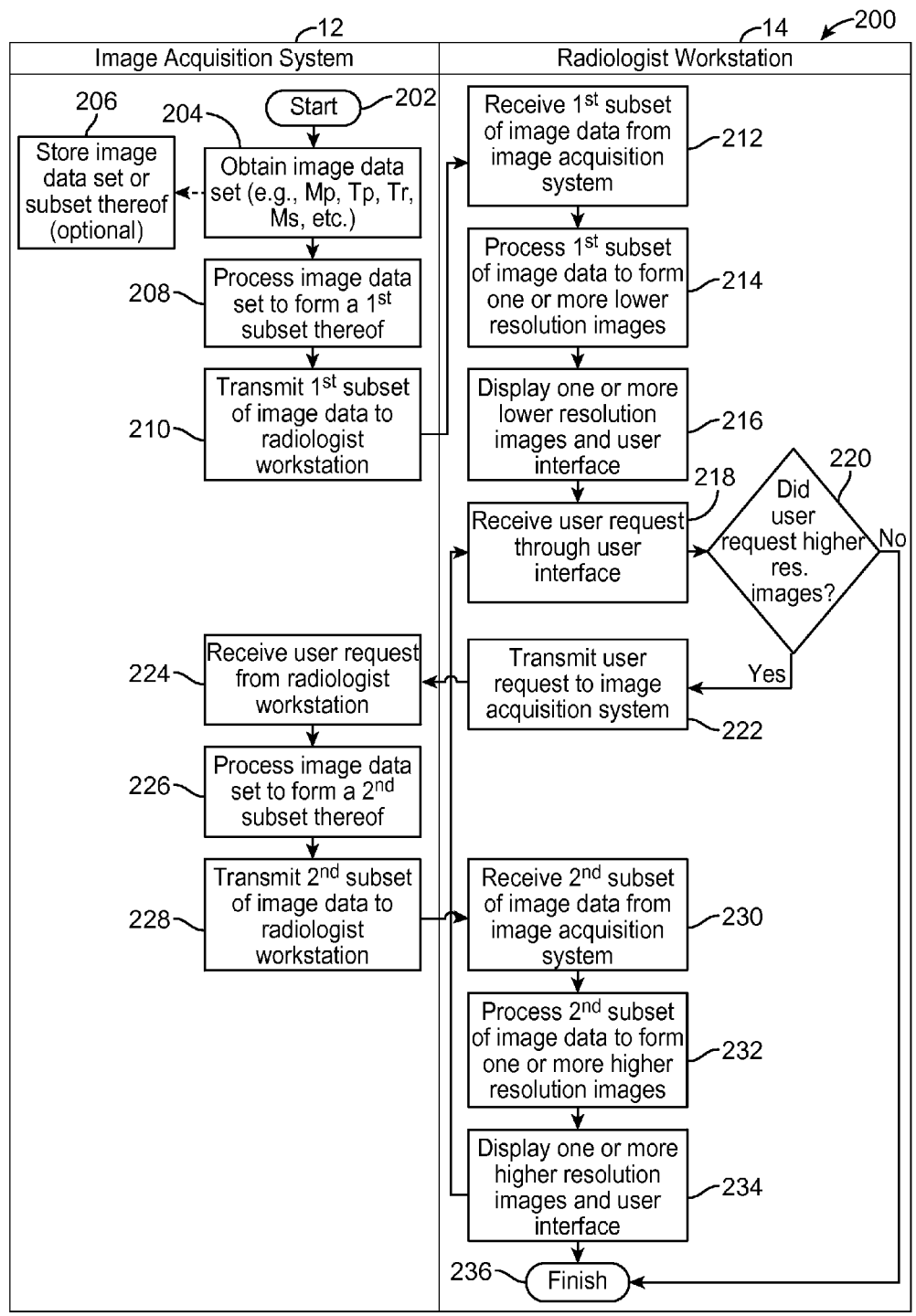
FIG. 3 is a flow diagram illustrating exemplary steps performed during a tomosynthesis image processing, communicating, and navigating method according to another embodiment.

FIG. 3 illustrates a method 200 for generating and reviewing a tomosynthesis data set according to another embodiment. The illustrated method 200 is similar to the method depicted in FIG. 2. However, in the method in FIG. 3, the radiologist workstation 14 carries out more of the image processing for display. This method is suitable for radiologist workstations 14 with more robust image processors.

The illustrated method begins at the "start" icon 202 on the flow chart. The image acquisition system 12 obtains an image data set at step 204. The image acquisition system 12 can optionally store the obtained image data set or a selected subset thereof in a memory module 22 at step 206. While no other storage of image data is depicted in FIG. 3, any of the subsets of image data can be stored in a memory module 22.

At step 208, the image acquisition system 12 processes the obtained image data set to form (generate) a first image data subset. This first image data subset is sufficient to describe one or more lower resolution images for display. However, the first image data subset generated at step 208 cannot be displayed without further processing.

At step 210, the image acquisition system 12 transmits the generated first image data subset to the radiologist workstation 14. At step 212, the radiologist workstation receives the transmitted first image data subset from the image acquisition system 12. At step 214, the radiologist workstation 14 processes the first image data subset to form one or more lower resolution images. At step 216, the radiologist workstation 14 displays the generated one or more lower resolution images, along with a user interface, on a display 30 to facilitate user interaction with the lower resolution image (detection images).

If the user requires higher resolution images for characterization of any detected FOIs, the user can provide a user request to the radiologist workstation 14. The radiologist workstation 14 receives the provided user request through the user interface at step 218. At step 220, the radiologist workstation 14 determines whether it has received a user request for one or more higher resolution images. If the radiologist workstation 14 did not receive such a request, the illustrated method concludes at the "finish" icon 236 on the flow chart. If the radiologist workstation 14 did receive a request for higher resolution images, the radiologist workstation 14 transmits the user request calling for higher resolution images to the image acquisition system 12 at step 222. The image acquisition system 12 receives the user request at step 224.

At step 226, the image acquisition system 12 generates a second image data subset from the image data set obtained in step 204 based on the received user request. Like the first image data subset, the second image data subset generated at step 226 cannot be displayed without further processing.

At step 228, the image acquisition system 12 transmits the generated second image data subset, in accordance with the user request, to the radiologist workstation 14. At step 230, the radiologist workstation 14 receives the transmitted second image data subset from the image acquisition system 12. At step 232, the radiologist workstation 14 processes the second image data subset to form one or more higher resolution images. At step 234, the radiologist workstation 14 displays the higher resolution images, along with a user interface, on a display to facilitate user interaction with the higher resolution image.

Using the displayed user interface, the user can make additional user requests for more higher resolution images, including, and up to, higher resolution images of the entire tomosynthesis volume. The radiologist workstation receives the user request at step 218. If the radiologist workstation determines whether it has received a user request for one or more higher resolution images at step 220, the higher resolution image generation, transmission, and display steps are repeated at steps 222, 224, 226, 228, 230, 232, and 234, until no further user requests are received. At that time, the illustrated method concludes at the "finish" icon 236 on the flow chart.

Like the method depicted in FIG. 2, the method depicted in FIG. 3 can also include highlighting of FOI during the generation of the first and second image data subsets.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall tomosynthesis image processing and navigating method may be achieved in a variety of manners using other image data processing methods known in the art. The system block diagrams are similarly representative only, illustrating functional delineations that are not to be viewed as limiting requirements of the disclosed inventions. Thus the above specific embodiments are illustrative, and many variations can be introduced on these embodiments without departing from the scope of the appended claims.

It will also be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A method for processing and communicating breast tissue image data, comprising:
   obtaining image data of a patient's breast tissue, the obtained image data having an acquired image resolution;
   processing the image data to form a first subset thereof, wherein the first subset of image data is configured to generate one or more lower resolution images of at least a portion of the patient's breast tissue, the one or more lower resolution images having a resolution lower than the acquired image resolution;
   transmitting the first subset of the image data to a user computer;
   receiving, from the user computer, a user request for higher resolution images of the patient's breast tissue that include a user identified feature, object or region in the one or more lower resolution images;
   in response to the received user request, further processing the image data to form a second subset thereof, wherein the second subset of the image data is configured to generate one or more higher resolution images of the patient's breast tissue that include the user identified feature, object or region, the one or more higher resolution images having a resolution that is higher than the resolution of the one or more lower resolution images; and
   transmitting the second subset of the image data to the user computer.

2. The method of claim 1, wherein the image data comprises acquired or synthesized X,Y coordinate slices at differing z axis locations of the patient's breast.

3. The method of claim 1, wherein a resolution of the one or more lower resolution images is sufficient to detect a potential abnormality or a region of interest in the patient's breast tissue.

4. The method of claim 1, wherein a resolution of the one or more higher resolution images is sufficient to characterize a potential abnormality or a region of interest in the patient's breast tissue.

5. The method of claim 1, wherein the resolution of the one or more higher resolution images is in the range of 50 microns to 85 microns.

6. The method of claim 5, wherein the resolution of the one or more higher resolution images is 70 microns.

7. The method of claim 1, wherein the resolution of the one or more higher resolution images is 1.5 times to 5 times the image resolution of the one or more lower resolution images.

8. The method of claim 7, wherein the resolution of the one or more higher resolution images is double the image resolution of the one or more lower resolution images.

9. The method of claim 1, wherein the image data comprises one or more images selected from a group consisting of tomosynthesis projection images, tomosynthesis reconstruction slices, mammography images, contrast enhanced mammography images, synthesized 2D images, and combinations thereof.

10. The method of claim 1, wherein the one or more low resolution images have a characteristic different from the characteristic of the one or more high resolution images, and wherein the characteristic is selected from the group consisting of slice thickness, pitch, yaw, and tilt.

11. A method for processing and communicating breast tissue image data, comprising:
    acquiring image data of a patient's breast tissue at an acquired image resolution;
    processing the acquired image data to form a first subset thereof, wherein the first subset of the acquired image data is configured to generate one or more lower resolution images of at least a portion of the patient's breast tissue, the one or more lower resolution images having a resolution lower than the acquired image resolution;
    transmitting the first subset of the acquired image data to a user computer;
    receiving, from the user computer, a user request for one or more higher resolution images corresponding to one or more of the one or more lower resolution images;
    in response to the received user request, processing the acquired image data to form a second subset thereof, wherein the second subset of the acquired image data is configured to generate the requested one or more higher resolution images, the one or more higher resolution images having a resolution that is higher than the resolution of the one or more lower resolution images but not higher than the acquired image resolution; and
    transmitting the second subset of the image data to the user computer.

12. The method of claim 11, wherein the acquired image data comprises X,Y coordinate slices at differing z axis locations of the patient's breast.

13. The method of claim 11, wherein a resolution of the one or more lower resolution images is sufficient to detect a potential abnormality or a region of interest in the patient's breast tissue.

14. The method of claim 11, wherein a resolution of the one or more higher resolution images is sufficient to characterize a potential abnormality or a region of interest in the patient's breast tissue.

15. The method of claim 11, wherein the resolution of the one or more higher resolution images is in the range of 50 microns to 85 microns.

16. The method of claim 11, wherein the resolution of the one or more higher resolution images is 70 microns.

17. The method of claim 11, wherein the resolution of the one or more higher resolution images is 1.5 times to 5 times the image resolution of the one or more lower resolution images.

18. The method of claim 11, wherein the resolution of the one or more higher resolution images is double the image resolution of the one or more lower resolution images.

19. The method of claim 11, wherein the image data comprises one or more images selected from a group consisting of tomosynthesis projection images, tomosynthesis reconstruction slices, mammography images, contrast enhanced mammography images, synthesized 2D images, and combinations thereof.

20. The method of claim 11, wherein the one or more low resolution images have a characteristic different from the characteristic of the one or more high resolution images, and wherein the characteristic is selected from the group consisting of slice thickness, pitch, yaw, and tilt.

21. A method for processing and communicating breast tissue image data, comprising:
    obtaining image data of a patient's breast tissue, the obtained image data having an acquired image resolution;
    processing the image data of the patient's breast tissue to form a first subset thereof, wherein the first subset of image data is configured to generate one or more lower resolution images of at least a portion of the patient's breast tissue in which a feature, object or region is automatically highlighted, the one or more lower resolution images having a resolution lower than the acquired image resolution;
    transmitting the first subset of the image data to a user computer;
    receiving, from the user computer, a user request for higher resolution images of the patient's breast tissue that include the automatically highlighted feature, object or region;
    in response to the received user request, processing the image data of the patient's breast tissue to form a second subset thereof, wherein the second subset of the image data is configured to generate one or more higher resolution images of the patient's breast tissue that include the automatically highlighted feature, object or region, the one or more higher resolution images having a resolution that is higher than the resolution of the one or more lower resolution images; and
    transmitting the second subset of the image data to the user computer.

22. The method of claim 21, wherein the acquired image data comprises X,Y coordinate slices at differing z axis locations of the patient's breast.

23. The method of claim 21, wherein a resolution of the one or more lower resolution images is sufficient to detect a potential abnormality or a region of interest in the patient's breast tissue.

24. The method of claim 21, wherein a resolution of the one or more higher resolution images is sufficient to characterize a potential abnormality or a region of interest in the patient's breast tissue.

25. The method of claim 21, wherein the resolution of the one or more higher resolution images is in the range of 50 microns to 85 microns.

26. The method of claim 21, wherein the resolution of the one or more higher resolution images is 70 microns.

27. The method of claim 21, wherein the resolution of the one or more higher resolution images is 1.5 times to 5 times the image resolution of the one or more lower resolution images.

28. The method of claim 21, wherein the resolution of the one or more higher resolution images is double the image resolution of the one or more lower resolution images.

29. The method of claim 21, wherein the image data comprises one or more images selected from a group consisting of tomosynthesis projection images, tomosynthesis reconstruction slices, mammography images, contrast enhanced mammography images, synthesized 2D images, and combinations thereof.

30. The method of claim 21, wherein the one or more low resolution images have a characteristic different from the characteristic of the one or more high resolution images, and wherein the characteristic is selected from the group consisting of slice thickness, pitch, yaw, and tilt.

\* \* \* \* \*